(12) United States Patent
Bernhardt, Jr.

(10) Patent No.: US 6,413,258 B1
(45) Date of Patent: Jul. 2, 2002

(54) ROD-TO-ROD COUPLER

(75) Inventor: Andrew E. Bernhardt, Jr., Alachua, FL (US)

(73) Assignee: Osteotech, Inc., Eatontown, NJ (US)

( * ) Notice: Subject to any disclaimer, the term of this patent is extended or adjusted under 35 U.S.C. 154(b) by 105 days.

(21) Appl. No.: 09/637,445

(22) Filed: Aug. 11, 2000

Related U.S. Application Data

(60) Provisional application No. 60/148,510, filed on Aug. 12, 1999.

(51) Int. Cl.$^7$ ................................................ A61B 17/56
(52) U.S. Cl. ........................................................ 606/61
(58) Field of Search .............................. 606/53, 61, 69, 606/70, 71; 24/712.5, 132 WL, 135 N, 115 K, 136 B; 403/186, 199, 403; 285/188; 248/62, 67.5, 68.1

(56) References Cited

U.S. PATENT DOCUMENTS

| | | | |
|---|---|---|---|
| 2,303,881 A | * | 12/1942 | Hubbard .................... 24/136 B |
| 2,346,346 A | | 4/1944 | Anderson |
| 4,258,708 A | | 3/1981 | Gentile |
| 4,502,473 A | | 3/1985 | Harris et al. |
| 4,570,625 A | | 2/1986 | Harris et al. |
| 4,611,580 A | | 9/1986 | Wu |
| 4,763,644 A | | 8/1988 | Webb |
| 4,895,141 A | | 1/1990 | Koeneman et al. |
| 4,920,959 A | | 5/1990 | Witzel et al. |
| 4,946,458 A | | 8/1990 | Harms et al. |
| 4,950,269 A | | 8/1990 | Gaines, Jr. |
| 4,988,349 A | | 1/1991 | Pennig |
| 5,002,542 A | | 3/1991 | Frigg |
| 5,024,213 A | | 6/1991 | Asher et al. |
| 5,041,113 A | | 8/1991 | Biedermann et al. |
| 5,042,982 A | | 8/1991 | Harms et al. |
| 5,067,955 A | | 11/1991 | Cotrel |
| 5,176,678 A | | 1/1993 | Tsou |
| 5,176,680 A | | 1/1993 | Vignaud et al. |
| 5,190,543 A | | 3/1993 | Schlapfer |
| 5,207,678 A | | 5/1993 | Harms et al. |
| 5,246,442 A | * | 9/1993 | Ashman et al. ................ 606/61 |
| 5,254,118 A | | 10/1993 | Mirkovic |
| 5,304,177 A | | 4/1994 | Pennig |
| 5,304,179 A | | 4/1994 | Wagner |
| 5,312,402 A | | 5/1994 | Schlapfer et al. |
| 5,312,404 A | | 5/1994 | Asher et al. |
| 5,330,473 A | | 7/1994 | Howland |
| 5,330,474 A | | 7/1994 | Lin |
| 5,342,360 A | | 8/1994 | Faccioli et al. |
| 5,344,422 A | | 9/1994 | Frigg |
| 5,405,347 A | | 4/1995 | Lee et al. |

(List continued on next page.)

FOREIGN PATENT DOCUMENTS

WO          9639090          12/1996

*Primary Examiner*—Todd E. Manahan
(74) *Attorney, Agent, or Firm*—Dilworth & Barrese, LLP

(57) ABSTRACT

A rod-to-rod coupler includes a body having first and second coupler portions. Each coupler portion defines a concavity configured to receive a portion of an elongated spinal rod. A screw and nut assembly which includes a screw and a flanged nut is positioned adjacent each concavity. Each flanged nut has a flange portion which extends at least partially over one concavity. After the rod-to-rod coupler has been positioned with the concavities located over adjacent spinal rods, the screw can be rotated to move the flanged nut into engagement with a spinal rod to secure the spinal rod within a concavity. In one embodiment, one coupler portion is formed with a blind bore and the other coupler portion is formed with an extension which is slidably received within the blind bore. The extension is slidable within the blind bore to selectively adjust the distance between the concavities of the first and second coupler portions. A set screw is provided to secure the extension at a fixed position within the blind bore.

10 Claims, 2 Drawing Sheets

U.S. PATENT DOCUMENTS

| | | | |
|---|---|---|---|
| 5,429,639 | A | 7/1995 | Judet |
| 5,443,467 | A | 8/1995 | Biedermann et al. |
| 5,466,237 | A | 11/1995 | Byrd, III et al. |
| 5,474,551 | A | 12/1995 | Finn et al. |
| 5,474,555 | A | 12/1995 | Puno et al. |
| 5,480,401 | A | 1/1996 | Navas |
| 5,480,442 | A | 1/1996 | Bertagnoli |
| 5,486,176 | A | 1/1996 | Hildebrand et al. |
| 5,501,684 | A | 3/1996 | Schlapfer et al. |
| 5,520,690 | A | 5/1996 | Errico et al. |
| 5,531,746 | A | 7/1996 | Errico et al. |
| 5,534,001 | A | 7/1996 | Schlapfer et al. |
| 5,549,608 | A | 8/1996 | Errico et al. |
| 5,554,157 | A | 9/1996 | Errico et al. |
| 5,569,247 | A | 10/1996 | Morrison |
| 5,582,612 | A * | 12/1996 | Lin .............................. 606/61 |
| 5,584,834 | A | 12/1996 | Errico et al. |
| 5,586,984 | A | 12/1996 | Errico et al. |
| 5,591,166 | A | 1/1997 | Bernhardt et al. |
| 5,601,551 | A | 2/1997 | Taylor et al. |
| 5,607,426 | A | 3/1997 | Ralph et al. |
| 5,628,740 | A | 5/1997 | Mullane |
| 5,647,873 | A | 7/1997 | Errico et al. |
| 5,662,648 | A | 9/1997 | Faccioli et al. |
| 5,662,651 | A | 9/1997 | Tornier et al. |
| 5,669,911 | A | 9/1997 | Errico et al. |
| 5,672,176 | A | 9/1997 | Biedermann et al. |
| 5,676,665 | A | 10/1997 | Bryan |
| 5,683,390 | A | 11/1997 | Metz-Stavenhagen et al. |
| 5,683,392 | A | 11/1997 | Richelsoph et al. |
| 5,690,630 | A | 11/1997 | Errico et al. |
| 5,725,527 | A | 3/1998 | Biedermann et al. |
| 5,733,285 | A | 3/1998 | Errico et al. |
| 5,746,741 | A | 5/1998 | Kraus et al. |
| 5,797,908 | A | 8/1998 | Meyers et al. |

* cited by examiner

ROD-TO-ROD COUPLER

This application claims priority from U.S. Provisional Application Serial No. 60/148,510 filed Aug. 12, 1999, which is incorporated herein by reference.

BACKGROUND

1. Technical Field

The present disclosure relates to a coupler for securing adjacent rods together in fixed relation. More specifically, the present disclosure relates to a rod-to-rod coupler for securing adjacent spinal rods together in fixed relation during spinal correction procedures.

2. Background of Related Art

Spinal rod systems for correcting and stabilizing spinal curvatures and for facilitating spinal fusion in surgical procedures to correct spinal disorders or degenerative conditions are well known in the art. Typically, these spinal rod systems include a plurality of bone fixation members and a pair of elongated spinal rods. The bone fixation members each have a first end which is secured to a vertebrae and a second end adapted to be fixedly connected to a spinal rod. During a spinal correction procedure, a plurality of fixation members are fixed to vertebrae at various points along the vertical length of the spine on each side of the spinal midline. Thereafter, each of the fixation members on each side of the spinal midline is linked with the other fixation members by one of the elongated spinal rods such that a spinal rod extends vertically along at least a portion of the length of the spine on each side of the spinal midline.

U.S. Pat. No. 5,683,392 to Richelsoph et al. ("the '392 patent") discloses a multi planar locking mechanism for securing a spinal rod to the spinal column. The '392 patent is incorporated herein by reference in its entirety.

Connector systems for transversely and rigidly connecting adjacent spinal rods together are also well known. Such connector systems are beneficial because they restrict spinal rod migration and increase the overall stiffness of the spinal rod system. In procedures involving multi-level fusion of the spine, a transverse connector system may be essential during the post operative period to minimize the amount of motion permitted between the spinal rods. By providing a rigid transverse connection between adjacent spinal rods, a stiffer construct can be created to enhance the promotion of spinal fusion.

U.S. Pat. No. 5,947,966 discloses a transverse connector system for linking adjacent spinal rods together. In one embodiment, the system includes first and second connector portions which are slidably adjustable in relation to each other. Each connector portion includes an engaging member configured to receive a spinal rod. A wedge member is provided in each engaging member to secure each connector portion to the spinal rod. The wedge member includes a screw for engaging and biasing the spinal rod into a receptacle defined by the engaging member. Because of the orientation of the wedge members with respect to the engaging member, it is sometimes difficult to position and secure a spinal rod within the receptacle of an engaging member.

Accordingly, a need exists for an improved spinal rod connector system which can be easily and quickly secured between adjacent spinal rods to provide a rigid stabilizing system.

SUMMARY

In accordance with the present disclosure, a rod-to-rod coupler is provided which includes a body having first and second coupler portion. Each coupler portion defines a concavity configured to receive a portion of an elongated spinal rod. A screw and nut assembly is positioned adjacent each concavity. Each screw and nut assembly includes a screw and a flanged nut. Each flanged nut has a flange portion which extends at least partially over a concavity. After the rod-to-rod coupler has been positioned with the concavities located over adjacent spinal rods, the screw can be rotated to move the flange nut into engagement with a spinal rod to secure the spinal rod within a concavity.

In an alternate embodiment, one coupler portion includes a blind bore and the other coupler portion includes an extension which is slidably received within the blind bore. The extension is slidable within the blind bore to selectively adjust the distance between the concavities of the first and second coupler portions. A set screw is provided to secure the extension at a fixed position within the blind bore.

BRIEF DESCRIPTION OF THE DRAWINGS

Various preferred embodiments of the rod-to-rod coupler are described herein with reference to the drawings, wherein.

DETAILED DESCRIPTION OF PREFERRED EMBODIMENTS

Figure 1:
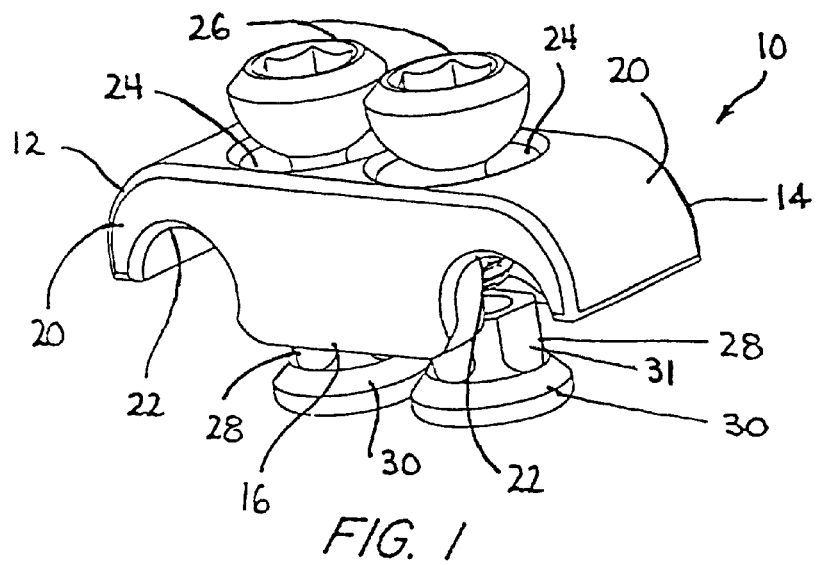
FIG. 1 is a perspective view of one embodiment of the presently disclosed rod-to-rod coupler.

Preferred embodiments of the presently disclosed rod-to-rod coupler will now be described in detail with reference to the drawings in which like reference numerals designate identical or corresponding elements in each of the several views.

Figure 1A:
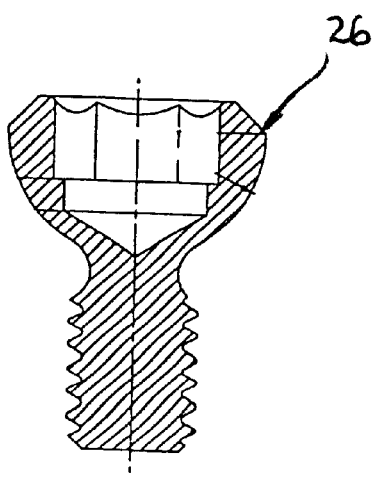
FIG. 1A is a cross-sectional view of the screw of the rod-to-rod coupler shown in FIG. 1.
Figure 1B:
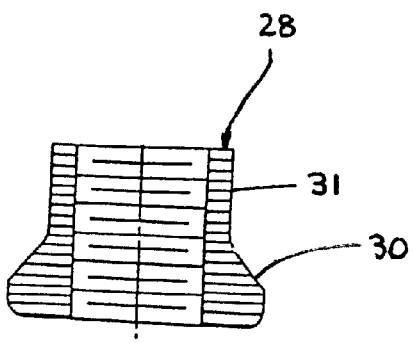
FIG. 1B is a cross-sectional view of the flanged nut of the rod-to-rod coupler shown in FIG. 1.

FIG. 1 illustrates one embodiment of the rod-to-rod coupler, shown generally as 10. Rod-to-rod coupler 10 includes a body having a first coupler portion 12, a second coupler portion 14 and a central body portion 16. First and second coupler portions 12 and 14 each include a curved section 20 defining a concavity 22. Each concavity 22 is dimensioned and configured to at least partially receive a spinal rod (not shown). A throughbore 24 which is dimensioned to receive a screw nut assembly is positioned adjacent to each of couplers 12 and 14. See FIGS. 1A and 1B. The screw nut assembly includes a screw 26 and a flanged nut 28. Screw 26 extends through throughbore 24 and is threadably engageable with flanged nut 28. Flanged nut 28 includes a flange portion 30 which is positioned at least partially below concavity 22 and a rectangular portion 31. Rectangular portion 31 is received in a correspondingly shaped portion of throughbore 24. The components of rod-to-rod coupler 10 can be constructed from any surgical grade material including stainless steel, plastics, ceramics, titanium, etc.

In use, first coupler 12 is secured to a first spinal rod by positioning concavity 22 adjacent the first spinal rod and, thereafter, rotating screw 26 in relation to flanged nut 28 to draw flange portion 30 of nut 28 into contact with the first spinal rod. The positioning of rectangular portion 31 of nut 28 in the correspondingly shaped portion of throughbore 24 prevents nut 28 from rotating with screw 26. As screw 26 is rotated, flanged nut 30 draws concavity 22 over a spinal rod and compresses the spinal rod into concavity 22 of first coupler 12. Thereafter, second coupler 14 is secured to a second spinal rod (not shown) in the same manner.

Figure 2:
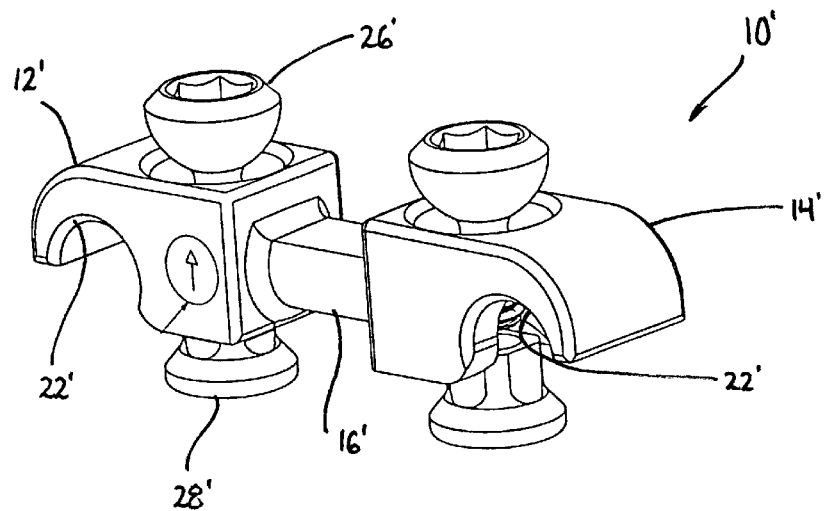
FIG. 2 is a perspective view of another embodiment of the presently disclosed rod-to-rod coupler.

FIG. 2 illustrates an alternate embodiment of the presently disclosed rod-to-rod coupler shown generally as 10'. Rod-to-rod coupler 10' is similar to rod-to-rod coupler 10 and includes a body having a first coupler portion 12', a second coupler portion 14' and a central body portion 16'. Each coupler portion 12' and 14' includes a concavity 22' configured and dimensioned to receive a spinal rod (not shown). A screw 26' and a flange nut 28' are associated with each concavity 22' to secure a spinal rod within the concavity. Rod-to-rod coupler 10' further includes an elongated central body portion 16'. The length of central body portion 16' may be selectively chosen to meet the requirement of a particular surgical procedure.

Figure 3:
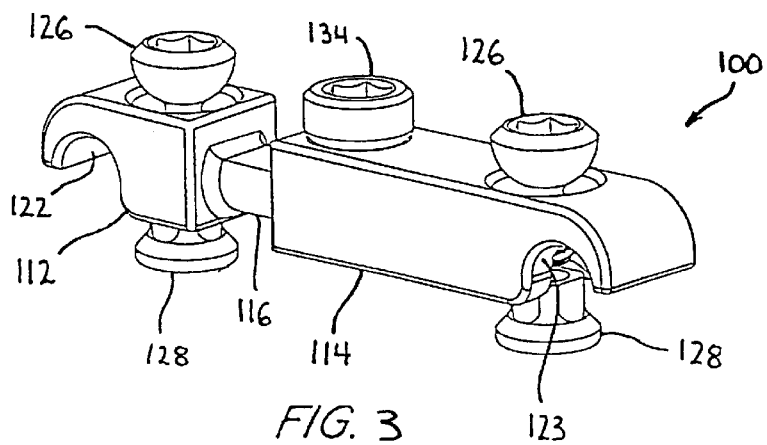
FIG. 3 is a perspective view of yet another embodiment of the presently disclosed rod-to-rod coupler.
Figure 4:
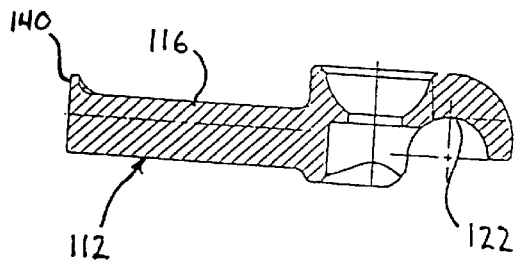
FIG. 4 is a side cross-sectional view of the first coupler portion of the rod-to-rod coupler shown in FIG. 3.
Figure 5:
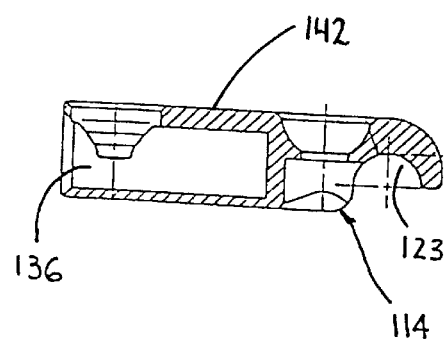
FIG. 5 is a side cross-sectional view of the second coupler portion of the rod-to-rod coupler shown in FIG. 3.

FIGS. 3–5 illustrate a second embodiment of the rod-to-rod coupler, shown generally as 100. Rod-to-rod coupler 100 includes a first adjustable coupler 112, a second adjustable coupler 114, a pair of screws 126, a pair of flange nuts 128 and a set screw 134. First coupler 112 includes a concavity 122 and an elongated extension 116. Concavity 122 is configured to receive a first spinal rod (not shown). The elongated extension 116 is configured to be slidably received within blind bore 136 (FIG. 3) formed in second coupler 114. Second coupler 114 includes a concavity 123 for receiving a second spinal rod (not shown), and a body 142 defining blind bore 136. Elongated extension 116 includes lip 140 formed at a distal end thereof. Lip 140 is positioned to engage set screw 134 when set screw 134 is positioned within throughbore 144. Engagement between lip 140 and set screw 134 prevents separation of first and second couplers 112 and 114.

In use, rod-to-rod coupler is positioned between spaced elongated rods (not shown). The distance between concavities 122 and 123 is adjusted by sliding extension 116 of coupler 112 within blind bore 136 formed in second coupler 114 until concavities 122 and 123 are positioned over respective spinal rods. Thereafter, couplers 112 and 114 are secured in fixed relation at a desired spacing by screwing set screw 20 into engagement with extension 116. To secure the elongated rods in concavities 122 and 123, screws 116 are rotated to draw flange nuts 118 into engagement with the elongated rods (not shown) to urge rods into concavities 122 and 123.

It will be understood that various modifications may be made to the embodiments disclosed herein. For example, the dimensions of the rod-to-rod coupler may vary to accommodate the particular patient and/or procedure being performed. Morever, the rod-to-rod coupler may be formed from a variety of different surgical grade materials including titanium, stainless steel, etc. Therefore, the above description should not be construed as limiting, but merely as exemplifications of preferred embodiments. Those skilled in the art will envision other modifications within the scope and spirit of the claims appended hereto.

Claims:

1. A rod-to-rod coupler comprising:

a body having a first coupler portion. and a second coupler portion, the first and second coupler portions defining first and second concavities, each concavity being configured and dimensioned to receive a rod; and a screw nut assembly supported adjacent each concavity, each screw and nut assembly including a screw and a flanged nut, the flanged nut having a flange positioned to at least partially cover one of the concavities.

2. A rod-to-rod coupler according to claim 1, further including an elongated central portion positioned between the first and second coupler portions, the elongated central portion maintaining the first and second coupler portions in fixed spaced relation.

3. A rod-to-rod coupler according to claim 1, wherein the body portion is formed of titanium.

4. A rod-to-rod coupler according to claim 1, wherein the body portion is formed of stainless steel.

5. A rod-to-rod coupler according to claim 1, wherein the first coupler portion is moveably supported in relation to the second coupler portion to selectively vary the distance between the first and second concavities.

6. A rod-to-rod coupler according to claim 5, wherein the first coupler portion defines a bore and the second coupler portion has an extension dimensioned to be slidably received within the bore.

7. A rod-to-rod coupler according to claim 6, wherein the first coupler portion defines an opening communicating with the bore, and further including a set screw dimensioned to extend through the bore into the opening.

8. A rod-to-rod coupler according to claim 6, wherein the extension of the second coupler portion has a projection formed thereon, the projection being positioned to engage the set screw when the set screw is positioned to extend through the opening.

9. A rod-to-rod coupler according to claim 6, wherein the body is formed of titanium.

10. A rod-to-rod coupler according to claim 6, wherein the body is formed of stainless steel.

* * * * *